US012773440B2

(12) United States Patent
Pfohl

(10) Patent No.: US 12,773,440 B2
(45) Date of Patent: Oct. 27, 2026

(54) SYNERGISTIC HERBAL COMPOSITIONS FOR PAIN MANAGEMENT AND OPIOID USE REDUCTION

(71) Applicant: Jeffrey L. Pfohl, San Antonio, TX (US)

(72) Inventor: Jeffrey L. Pfohl, San Antonio, TX (US)

( * ) Notice: Subject to any disclaimer, the term of this patent is extended or adjusted under 35 U.S.C. 154(b) by 234 days.

(21) Appl. No.: 18/759,816

(22) Filed: Jun. 29, 2024

(65) Prior Publication Data

US 2026/0000726 A1 Jan. 1, 2026

(51) Int. Cl.

| | |
|---|---|
| ***A61K 36/00*** | (2006.01) |
| ***A61K 31/00*** | (2006.01) |
| ***A61K 31/09*** | (2006.01) |
| ***A61K 31/198*** | (2006.01) |
| ***A61K 31/352*** | (2006.01) |
| ***A61K 31/4525*** | (2006.01) |
| ***A61K 31/7048*** | (2006.01) |
| ***A61K 36/185*** | (2006.01) |
| ***A61K 36/489*** | (2006.01) |
| ***A61K 36/539*** | (2006.01) |
| ***A61K 36/67*** | (2006.01) |
| ***A61K 36/74*** | (2006.01) |
| ***A61K 36/9066*** | (2006.01) |

(52) U.S. Cl.

CPC .............. *A61K 36/67* (2013.01); *A61K 31/09* (2013.01); *A61K 31/198* (2013.01); *A61K 31/352* (2013.01); *A61K 31/4525* (2013.01); *A61K 31/658* (2023.05); *A61K 31/7048* (2013.01); *A61K 36/3482* (2024.05); *A61K 36/489* (2013.01); *A61K 36/539* (2013.01); *A61K 36/74* (2013.01); *A61K 36/9066* (2013.01)

(58) Field of Classification Search

CPC .................................................. A61K 36/3482

See application file for complete search history.

(56) References Cited

U.S. PATENT DOCUMENTS

2007/0087977 A1* 4/2007 Robbins ............... A61K 31/445 514/23

* cited by examiner

*Primary Examiner* — Qiuwen Mi

(74) *Attorney, Agent, or Firm* — Sam Pierce

(57) ABSTRACT

Pharmaceutical compositions comprising synergistic combinations of herbal compounds from *Mitragyna speciosa, Piper methysticum, Curcuma longa, Scutellaria baicalensis, Piper nigrum, Cannabis sativa, Camellia sinensis, Sophora japonica*, and optionally *Valeriana officinalis* and 4-amino-3-phenylbutanoic acid are provided for treating pain and reducing opioid use. The compositions comprise defined ratios of the extracts optimized for enhanced analgesic efficacy and opioid-sparing effects. Methods of administering the compositions to subjects in need thereof result in significant reductions in pain and opioid use compared to the individual components. The unique multi-component formulations take advantage of synergistic interactions between extracts with analgesic, anxiolytic, and opioid use disorder mitigating properties.

12 Claims, 2 Drawing Sheets

SYNERGISTIC HERBAL COMPOSITIONS FOR PAIN MANAGEMENT AND OPIOID USE REDUCTION

BACKGROUND

The present invention relates to pharmaceutical compositions comprising herbal compounds for the treatment of pain and reduction of opioid use. More specifically, the invention provides compositions containing *Mitragyna speciosa* (kratom), *Piper methysticum* (kava), *Curcuma longa* (turmeric), *Scutellaria baicalensis* (Chinese skullcap), *Piper nigrum* (black pepper), *Cannabis sativa, Camellia sinensis* (green tea), *Sophora japonica, Valeriana officinalis* (valerian), and 4-amino-3-phenylbutanoic acid (phenibut) that are effective in reducing pain, inflammation, and opioid use when administered to a subject in need thereof.

Pain is a major health problem that affects millions of people worldwide. Opioids are commonly prescribed for the treatment of moderate to severe pain, but their use is associated with significant adverse effects, including addiction, tolerance, and overdose. The pharmaceutical industry has been working on opioid alternatives for decades with limited success[1]. Thus there is an urgent need for alternative pain management strategies that can reduce reliance on opioids while still providing effective analgesia.

Historically, pharmaceutical research has focused on developing highly selective molecules that bind with high affinity to a single biological target. This approach, prevalent until the early 2000s, has not yielded effective alternatives to opioids for pain management. However, since approximately 2010, there has been a gradual shift towards a systems biology approach in drug discovery. This approach takes a more holistic view of disease, targeting multiple biological pathways to mitigate disease states. Despite the potential advantages of this method, its adoption has been slow, with an estimated 10-20% of pharmaceutical research projects employing this approach, resulting in only a small number of approved drugs[2].

Herbal medicines and natural product-derived drugs, which contain active compounds isolated from herbs, possess a unique advantage in the treatment of diseases and health conditions. By nature, these compounds typically impact multiple biological targets, often within pathways that are relevant to a particular disease or health state. This multi-target approach has been leveraged by traditional medicine for centuries to treat various health conditions. More recently, natural product-derived drugs have been investigated for their potential in treating pain and addiction. For example, WO 02/094297 A1 discloses an herbal composition comprising borax, ginseng, gentian root, and chicken gallbladder extract for the treatment of drug addiction and insomnia. The composition may optionally include additional herbs such as oyster shell, white peony, rhubarb, ginger, and licorice.

*Mitragyna speciosa*, also known as kratom, is a tropical tree native to Southeast Asia. The leaves of the plant contain several alkaloids, including mitragynine and 7-hydroxymitragynine, which act as partial agonists at the mu-opioid receptor and produce analgesic and opioid-like effects. Kratom has been used traditionally as a stimulant and pain reliever, and more recently as an opioid substitute to manage withdrawal symptoms. However, the safety and efficacy of kratom for these indications has not been well established.

Cannabidiol (CBD) is a non-psychoactive cannabinoid derived from *Cannabis sativa*. CBD has anti-inflammatory, antioxidant, anxiolytic, and analgesic properties mediated by modulation of the endocannabinoid system, TRP channels, serotonin receptors, and other targets. Preclinical studies indicate CBD reduces neuropathic, inflammatory, and cancer pain. Clinical trials suggest CBD, alone or in combination with THC, may be effective for chronic pain, especially neuropathic pain.

L-theanine is an amino acid found in green tea (*Camellia sinensis*). L-theanine promotes relaxation and reduces stress and anxiety by increasing alpha brain wave activity and modulating neurotransmitters such as GABA, serotonin, and dopamine. L-theanine has been shown to potentiate the analgesic effects of morphine and reduce opioid dependence in animal models, but human data is scarce.

Phenibut (4-amino-3-phenylbutanoic acid) is a synthetic GABA analogue used as a nootropic and anxiolytic agent. Phenibut binds to GABAB receptors and stimulates dopamine receptors, leading to reduced anxiety, improved sleep, and enhanced cognition. Phenibut has been shown to potentiate the effects of opioids and reduce opioid dependence in rodents, but controlled studies in humans are lacking.

In summary, while a variety of herbal medicines have shown promise for the treatment of pain and opioid addiction, there remains a need for novel compositions that can provide safe and effective analgesia while reducing the need for opioids. The present invention addresses this need by providing unique combinations of herbal compounds with synergistic effects on pain and opioid use reduction.

SUMMARY

The present invention provides pharmaceutical compositions and methods for treating pain and reducing opioid use in a subject in need thereof. The compositions comprise synergistic combinations of herbal compounds including *Mitragyna speciosa* (kratom), *Piper methysticum* (kava), *Curcuma longa* (turmeric), *Scutellaria baicalensis* (Chinese skullcap), *Piper nigrum* (black pepper), *Cannabis sativa, Camellia sinensis* (green tea), *Sophora japonica*, and optionally *Valeriana officinalis* (valerian) and 4-amino-3-phenylbutanoic acid (phenibut). The compounds may be obtained from the whole herb or as extracts or powders from the herb species selected from the group listed.

In one aspect, the invention provides a pharmaceutical composition comprising: a) 0.5 to 2.5 grams of Red Borneo Kratom or Red Bali Kratom; b) 0.5 to 2.5 grams of Green Maeng Da Kratom or Green Malay Kratom; c) 0.5 to 2.5 grams of Kava root from the Vanuatu strain; d) 0.5 to 2.5 grams of Curcumin or a Curcumin extract; e) 0.1 to 1.0 grams of Baicalin or a Baicalin extract; f) 5 to 25 milligrams of Piperine or a Piperine extract; g) 10 to 100 milligrams of Cannabidiol (CBD) or a CBD extract; h) 100 to 800 milligrams of L-Theanine; and i) 100 to 600 milligrams of Quercetin or a Quercetin extract. The composition is formulated for oral administration in an amount effective to reduce pain and opioid use.

In some embodiments, the composition further comprises 250-750 mg of Phenibut and 250-750 mg of Valerian root extract for nighttime administration. The composition may be formulated as a powder, tablet, capsule, softgel, liquid solution, or suspension. A dose-response titration starting at 1-3 teaspoons and increasing by 0.1-0.5 teaspoon increments can be used to achieve a therapeutically effective reduction in pain.

Administration of the composition can reduce opioid use by at least 25-75% and reduce pain by at least 25-75% as measured by a visual analog scale compared to baseline. The composition may also reduce symptoms of opioid withdrawal, anxiety, and improve sleep quality.

In another aspect, a method is provided for reducing pain and opioid use comprising administering an effective amount of a composition comprising: a) 0.5-2.5 grams of a first *Mitragyna speciosa* powder; b) 0.5-2.5 grams of a second *Mitragyna speciosa* powder different from the first; c) 0.5-2.5 grams of a *Piper methysticum*; d) 0.5-2.5 grams of a *Curcuma longa* extract; e) 0.1-1.0 grams of a *Scutellaria baicalensis* extract; f) 5-50 milligrams of a *Piper nigrum* extract; g) 10-100 milligrams of a *Cannabis sativa* extract; h) 100-600 milligrams of L-theanine; i) 100-500 milligrams of a *Sophora japonica* extract; and optionally j) 100-1000 milligrams each of phenibut and *Valeriana officinalis* extract. The ratio of components a) through i) is optimized for synergistic effects. Administration of the composition results in at least a 30-60% reduction in pain and enables a reduction or elimination of opioid use.

The compositions of the invention are based on the unexpected discovery that certain combinations of herbal extracts or herbal powders, at defined ratios, provide enhanced analgesic efficacy and enable significant reductions in opioid use compared to the individual components. The use of different *Mitragyna speciosa* strains allows tailoring the effects for daytime or nighttime use. The addition of piperine increases the bioavailability and efficacy of the other ingredients.

In summary, the present invention fulfills the need for an effective natural alternative for managing pain and reducing the burden of opioid use disorders. The unique multi-component compositions take advantage of the synergistic interactions between herbal extracts or powders with analgesic, anxiolytic, and opioid-sparing properties.

Additional features and advantages of the invention will be set forth in the description which follows, and in part will be obvious from the description, or may be learned by the practice of the invention. These and other features of the present invention will become more fully apparent from the following description, or may be learned by the practice of the invention as set forth hereinafter.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

Figure 1:
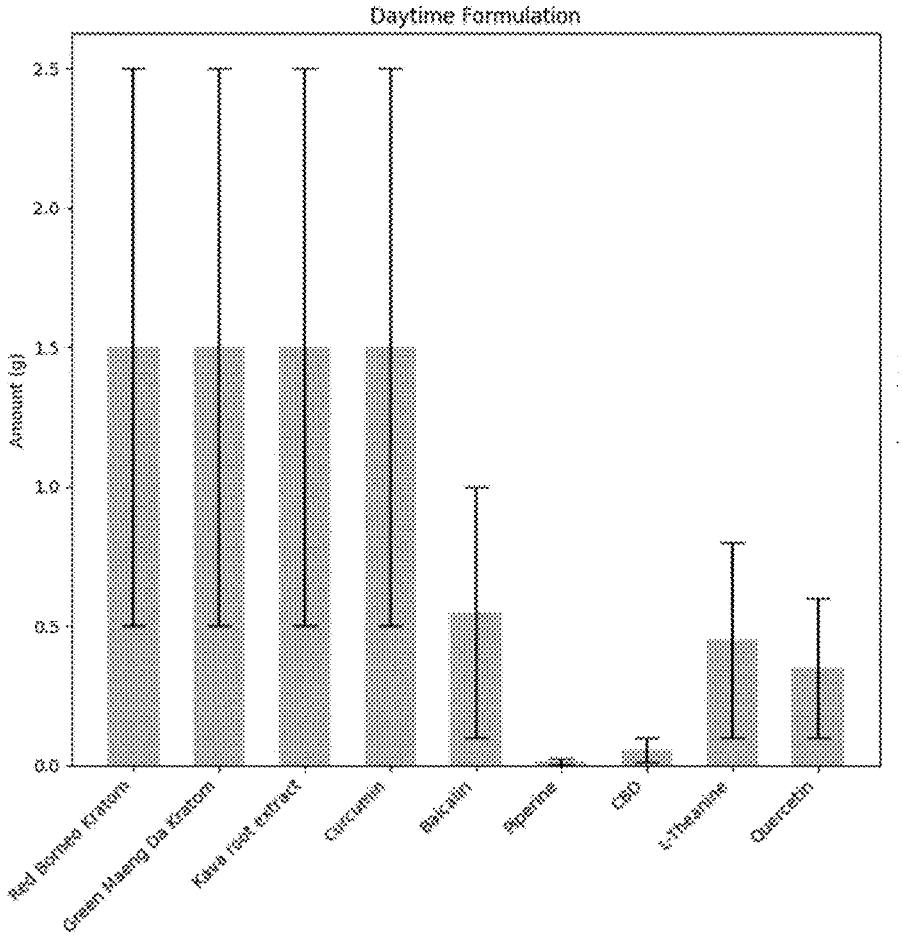
FIG. 1 is a bar graph depicting the relative amounts of each ingredient in a daytime formulation of the pharmaceutical composition

In the following detailed description of the preferred embodiments, reference is made to the accompanying drawings, which form a part hereof and show, by way of illustration, specific embodiments in which the invention may be practiced. It is to be understood that other embodiments may be used and structural or logical changes may be made without departing from the scope of the present invention. The following detailed description, therefore, is not to be taken in a limiting sense, and the scope of the present invention is defined by the appended claims.

The following description is provided as an enabling teaching of the present systems, and/or methods in its best, currently known aspect. To this end, those skilled in the relevant art will recognize and appreciate that many changes can be made to the various aspects of the present systems described herein, while still obtaining the beneficial results of the present disclosure. It will also be apparent that some of the desired benefits of the present disclosure can be obtained by selecting some of the features of the present disclosure without utilizing other features.

Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

The terms "a" and "an" and "the" and similar references used in the context of describing a particular embodiment of the present invention (especially in the context of certain claims) are construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein.

All systems described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application. Thus, for example, reference to "an element" can include two or more such elements unless the context indicates otherwise.

As used herein, the terms "optional" or "optionally" mean that the subsequently described event or circumstance can or cannot occur, and that the description includes instances where said event or circumstance occurs and instances where it does not.

The word or as used herein means any one member of a particular list and also includes any combination of members of that list. Further, one should note that conditional language, such as, among others, "can," "could," "might", or "may" unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular aspect.

The present invention relates to compositions and methods for reducing pain and opioid use in subjects in need thereof. The compositions comprise specific ratios of extracts from *Mitragyna speciosa, Piper methysticum, Curcuma longa, Scutellaria baicalensis, Piper nigrum, Cannabis sativa, Sophora japonica*, and optionally *Valeriana officinalis*, along with L-theanine and optionally 4-amino-3-phenylbutanoic acid (phenibut). The compositions further comprise specific ratios of powders from *Mitragyna spe-*

*ciosa, Piper methysticum, Curcuma longa, Scutellaria baicalensis, Piper nigrum, Cannabis sativa, Sophora japonica*, and optionally *Valeriana officinalis*, along with L-theanine and optionally 4-amino-3-phenylbutanoic acid (phenibut). The compositions further comprise specific ratios of extracts, and powders from *Mitragyna speciosa, Piper methysticum, Curcuma longa, Scutellaria baicalensis, Piper nigrum, Cannabis sativa, Sophora japonica*, and optionally *Valeriana officinalis*, along with L-theanine and optionally 4-amino-3-phenylbutanoic acid (phenibut).

The *Mitragyna speciosa* powders used in the compositions are selected from Red Borneo Kratom, Green Maeng Da Kratom, Red Bali Kratom, and Green Malay Kratom. Two different *Mitragyna speciosa* powders are included in each composition. The extracts are obtained from the leaves of the *Mitragyna speciosa* plant. Each *Mitragyna speciosa* powder is included in an amount from 0.5-2.5 grams.

The compositions further contain a *Piper methysticum* from a Vanuatu strain. The *Piper methysticum* is obtained from the roots of a *Piper methysticum* plant of the Vanuatu strain and is included in an amount from 0.5-2.5 grams.

A *Curcuma longa* extract comprising 50-95%, preferably 70-95%, curcuminoids is also included in the compositions in an amount from 0.5-2.5 grams.

The compositions additionally contain a *Scutellaria baicalensis* extract comprising 30-90% baicalin in an amount from 0.1-1.0 grams.

A *Piper nigrum* extract comprising 85-99% piperine is included in the compositions in an amount from 5-50 milligrams.

The compositions also contain a *Cannabis sativa* extract comprising 90-99.9% cannabidiol (CBD) in an amount from 10-100 milligrams.

L-theanine is included in the compositions in an amount from 100-600 milligrams

A *Sophora japonica* extract comprising 85-99% quercetin is also included in an amount from 100-500 milligrams.

Optionally, the compositions may further contain 100-1000 milligrams of 4-amino-3-phenylbutanoic acid (phenibut) and 100-1000 milligrams of a *Valeriana officinalis* extract.

In another embodiment 200-800 milligrams of EGCG (Epigallocatechin Gallate) extract from green tea, 30-60% purity and 200-1600 milligrams of N-Acetyl L-Cysteine are also included in the formulation.

In the compositions, the ratio of the first *Mitragyna speciosa* powder to the second *Mitragyna speciosa* powder to the *Piper methysticum* to the *Curcuma longa* extract to the *Scutellaria baicalensis* extract to the *Piper nigrum* extract to the *Cannabis sativa* extract to the L-theanine to the *Sophora japonica* extract is 1:1:1:1:0.2-0.8:0.01-0.1:0.02-0.2:0.2-1.2:0.2-1 by weight. In a preferred embodiment, the ratio is 2.5:2.5:2.5:2.5:1:0.024:0.1:0.8:0.6 by weight.

The compositions are formulated for oral administration as powders, tablets, capsules, or liquid suspensions. A typical dosing regimen is administration 1 to 6 times per day. In one embodiment, the composition is administered in a dose of 1 to 6 teaspoons. The dose may be increased by ⅛ to ½ teaspoon increments until no further reduction in pain is achieved.

Administration of the compositions to a subject in need thereof results in at least a 30-60%, or 30-70%, reduction in pain as measured by a visual analog scale. The compositions also enable a reduction or elimination of opioid use by the subject. In some embodiments, the reduction or elimination of opioid use treats an opioid addiction in the subject The compositions have additional benefits when administered to subjects. Administration results in at least a 30-70% reduction in anxiety. The compositions also decrease an area of hypersensitivity to touch (allodynia) by at least 50-80%. In subjects with a cold limb, administration of the composition normalizes the temperature of the limb. The compositions also reduce pain in the teeth of subjects.

The present invention provides a novel and beneficial combination of herbal medicines and natural product drugs that target multiple pathways involved in pain: transduction (sensing), transmission, perception, inflammation, and addiction. By impacting these pathways simultaneously, the invention is able to mitigate nociceptive, neuropathic, and oncoplastic pain while facilitating the discontinuation of addictive drugs.

A key aspect of the invention is the overlap in targets of the individual active components found in the herbal medicines and natural product drugs. For instance, both quercetin and curcumin inhibit the COX1 enzyme, while curcumin, CBD, and baicalin impact the nociceptive receptor TRPV1 (see Tables X-Y). This overlap allows for synergistic effects on the same target, thereby increasing the overall efficacy of the composition.

One example of this synergistic effect is the inhibition of COX1 by quercetin and curcumin. Studies have shown that these two compounds work synergistically to inhibit COX1[3], and docking studies have further demonstrated their synergistic binding[4]. Another example is the inhibition of TRPV1 by baicalin and catechin. At a concentration of 25 μM, baicalin inhibits TRPV1 by 31.2%, while catechin inhibits TRPV1 by 28.7% at the same concentration. When combined, however, they inhibit TRPV1 with an efficacy of 76%[5].

By leveraging the overlapping targets and synergistic effects of the active components in the herbal medicines and natural product drugs, the present invention provides a novel and effective approach to managing various types of pain while reducing the reliance on addictive drugs.

In one embodiment, the *Mitragyna speciosa, Piper methysticum*, and *Voacanga africana* components are included as the whole herb rather than as an extract. While extracts of these herbs can be used, the whole herb is preferred in order to capture the full breadth of alkaloids present. The *Mitragyna speciosa* whole herb is included in an amount from 1-5 grams, the *Piper methysticum* whole herb is included in an amount from 1-5 grams, and the *Voacanga africana* root bark whole herb is included in an amount from 100-500 mg.

In a further embodiment, the composition is formulated for treating addiction, including opioid addiction and addiction to other substances such as tetrahydrocannabinol (THC). This embodiment further comprises 500-750 mg of a *Passiflora incarnata* extract, 400-600 mg of a *Rhodiola rosea* extract, 500-750 mg of a *Magnolia officinalis* extract, and 400-600 mg of a *Mucuna pruriens* extract and 100-500 mg of *Voacanga Africana* root bark.

An additional embodiment is formulated for treating migraine headaches. This embodiment further comprises 2-3 grams of *Salix alba* bark whole herb, 1.5-2.5 grams of a *Coffea canephora* extract, and 500-750 mg of a *Petasites hybridus* extract. The *Salix alba* provides salicin to reduce inflammation and pain, the *Coffea canephora* provides caffeine to constrict blood vessels and relieve migraine pain, and the *Petasites hybridus* provides petasin to reduce spasms and inflammation.

The compositions of the present invention are formulated and administered to provide an effective amount of each active ingredient. An "effective amount" means an amount of an active ingredient that, when administered to a subject for treating a state, disorder or condition, is sufficient to effect such treatment. The "effective amount" will vary depending on the ingredient, the state, disorder, or condition being treated, the severity of the state, disorder, or condition, the age and physical condition of the subject, the route of administration, and the like.

The compositions are formulated into any suitable oral dosage form, including powders, granules, tablets, capsules, liquids, suspensions, emulsions, syrups, elixirs, and the like. The compositions can be formulated as immediate release, sustained release, or controlled release dosage forms using standard excipients and manufacturing techniques known in the art.

In an exemplary embodiment the doses are administered in liquid form from extraction with hot water and lemon juice.

The compositions are administered one to six times per day, preferably two to four times per day. A typical dose is 1-6 teaspoons of the powder or granules, 1-6 tablets, or 1-6 capsules. The dose is preferably administered 30-60 minutes before meals. The dose can be titrated up in ⅛ to ½ teaspoon increments until the desired therapeutic effect is achieved.

FIG. 1 is a bar graph depicting the relative amounts of each ingredient in a daytime formulation of the pharmaceutical composition. The y-axis shows the ingredient names and the x-axis shows the amount ranges in grams or milligrams.

Bar (a) represents Red Borneo Kratom, which is present in an amount ranging from 0.5 to 2.5 grams. Red Borneo Kratom is a strain of *Mitragyna speciosa* known for its pain-relieving and energizing effects, making it suitable for daytime use.

Bar (b) shows Green Maeng Da Kratom, another strain of *Mitragyna speciosa*, which is included in the composition in an amount ranging from 0.5 to 2.5 grams. Green Maeng Da Kratom is recognized for its balanced effects, providing pain relief and increased alertness without excessive sedation.

Bar (c) depicts Kava root, specifically from the Vanuatu strain of *Piper methysticum*, in an amount ranging from 0.5 to 2.5 grams. Kava root has anxiolytic and analgesic properties that complement the effects of the Kratom strains.

Bar (d) represents Curcumin, a polyphenolic compound derived from *Curcuma longa*, in an amount ranging from 0.5 to 2.5 grams. Curcumin possesses potent anti-inflammatory and antioxidant properties that can help alleviate pain and reduce opioid requirements.

Bar (e) shows Baicalin, a flavone glycoside extracted from *Scutellaria baicalensis* root, in an amount ranging from 0.1 to 1.0 grams. Baicalin has been shown to exhibit anti-inflammatory, analgesic, and neuroprotective effects.

Bar (f) represents Piperine, an alkaloid derived from *Piper nigrum* fruit, in an amount ranging from 5 to 25 milligrams. Piperine is included as a bioavailability enhancer, improving the absorption and efficacy of the other ingredients.

Bar (g) depicts Cannabidiol (CBD), a non-psychoactive cannabinoid obtained from *Cannabis sativa*, in an amount ranging from 10 to 100 milligrams. CBD has been demonstrated to possess analgesic, anti-inflammatory, and anxiolytic properties, making it a valuable addition to the composition.

Bar (h) shows L-Theanine, an amino acid found in *Camellia sinensis*, in an amount ranging from 100 to 800 milligrams. L-Theanine promotes relaxation and reduces stress and anxiety without causing drowsiness, thereby supporting the overall therapeutic effects of the composition.

Finally, bar (i) represents Quercetin, a flavonoid extracted from *Sophora japonica*, in an amount ranging from 100 to 600 milligrams. Quercetin has anti-inflammatory and antioxidant properties that can help reduce pain and inflammation.

Figure 2:
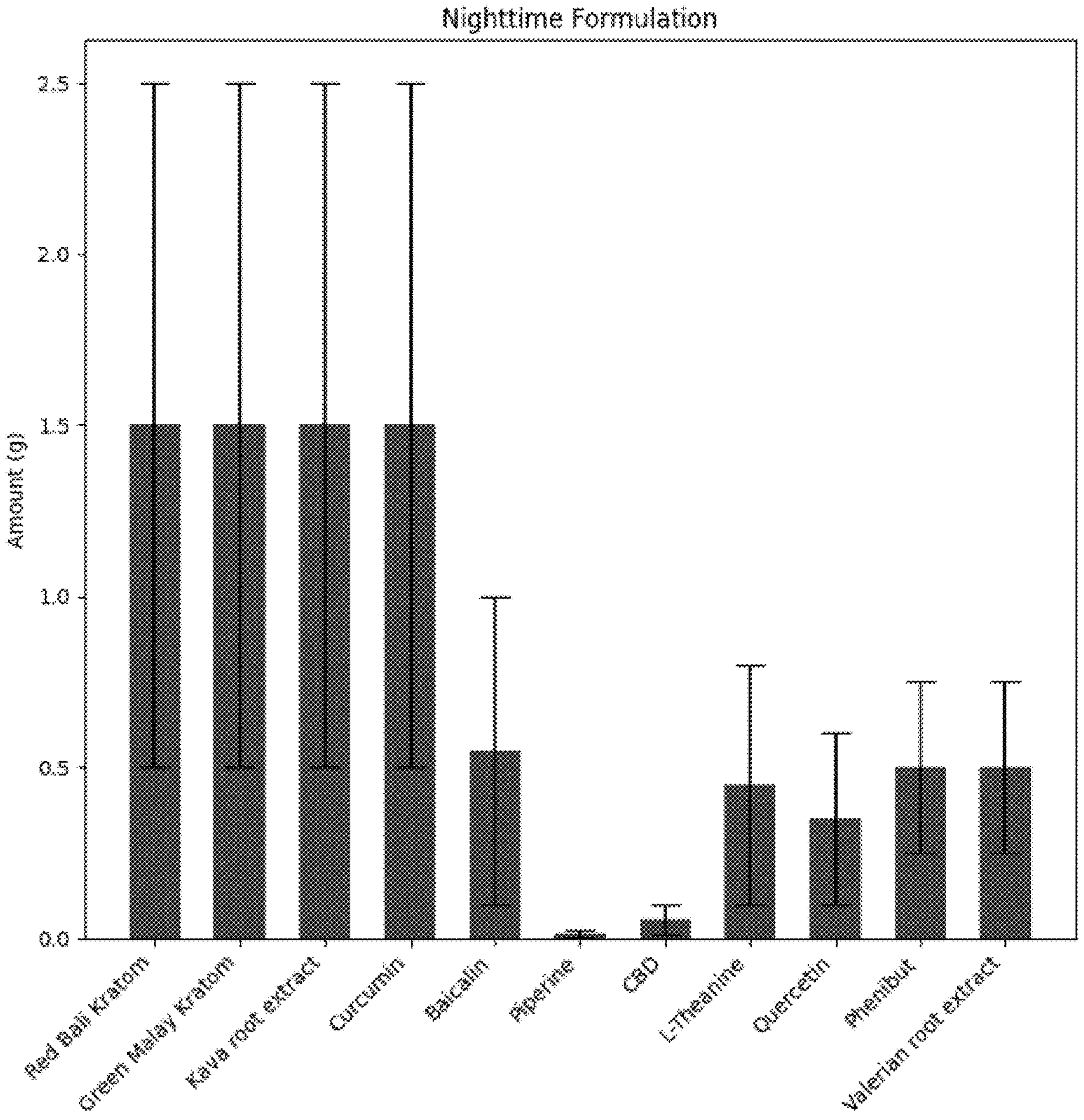
FIG. 2 is a bar graph depicting the relative amounts of each ingredient in a nighttime formulation of the pharmaceutical composition.

FIG. 2 is a bar graph depicting the relative amounts of each ingredient in a nighttime formulation of the pharmaceutical composition. The y-axis shows the ingredient names while the x-axis indicates the amount ranges in grams (g) or milligrams (mg).

The first two ingredients, Red Bali Kratom and Green Malay Kratom, are each present in an amount ranging from 0.5 g to 2.5 g. Red Bali Kratom and Green Malay Kratom are *Mitragyna speciosa* powders included in the nighttime formulation to provide pain relief and sleep induction effects.

Kava root, obtained from the Vanuatu strain of *Piper methysticum*, is included in an amount from 0.5 g to 2.5 g. Curcumin, a curcuminoid extract from *Curcuma longa*, is present in the same amount range of 0.5 g to 2.5 g.

Baicalin, an extract from the root of *Scutellaria baicalensis*, is present in an amount from 0.1 g to 1.0 g. Piperine, extracted from the fruit of *Piper nigrum*, is included in a lower amount ranging from 5 mg to 25 mg.

Cannabidiol (CBD), an extract from *Cannabis sativa*, is present in an amount from 10 mg to 100 mg. L-Theanine, an amino acid, is included in a higher amount ranging from 100 mg to 800 mg.

Quercetin, a flavonoid extract from *Sophora japonica*, is present in an amount from 100 mg to 600 mg.

The last two ingredients are Phenibut and Valerian root extract, each included in an amount ranging from 250 mg to 750 mg. Phenibut is the common name for 4-amino-3-phenylbutanoic acid. The Valerian root extract is obtained from *Valeriana officinalis*. The inclusion of Phenibut and Valerian root extract in these amounts makes the composition especially suited for nighttime administration to improve sleep quality.

In one embodiment, the first *Mitragyna speciosa* powder in the daytime formulation is Red Borneo Kratom and the second *Mitragyna speciosa* powder in the daytime formulation is Green Maeng Da Kratom. The first *Mitragyna speciosa* powder in the nighttime formulation is Red Bali Kratom and the second *Mitragyna speciosa* powder in the nighttime formulation is Green Malay Kratom. These specific strains of *Mitragyna speciosa* are selected for their respective energizing or sedating properties to optimize the composition for daytime or nighttime use.

In another embodiment, the nighttime formulation further comprises 100-1000 milligrams of 4-amino-3-phenylbutanoic acid (phenibut) and 100-1000 milligrams of a *Valeriana officinalis* extract. The inclusion of phenibut and Valerian root extract in these amounts enhances the sleep-promoting effects of the nighttime formulation.

Administration of the composition may reduce pain in various parts of the body, including the teeth of the subject. The reduction or elimination of opioid use achieved through the use of this composition may also treat an opioid addiction in the subject.

The composition may be administered in a dose-response titration, starting at a low dose and gradually increasing until the desired therapeutic effect is achieved. In one embodiment, the starting dose is 1-3 teaspoons, and the dose is increased by ⅛ to ½ teaspoon increments until no further reduction in pain is achieved.

The *Piper nigrum* extract used in the composition may be standardized to contain at least 85-99% piperine, the active compound responsible for its bioavailability-enhancing effects. Similarly, the *Cannabis sativa* extract may be standardized to contain at least 90-99.9% cannabidiol (CBD), and the *Sophora japonica* extract may be standardized to contain at least 85-99% quercetin.

The *Scutellaria baicalensis* extract used in the composition may be standardized to contain at least 30-90% baicalin, and the *Curcuma longa* extract may be standardized to contain 70-95% curcuminoids. Standardization ensures consistent potency and therapeutic effects across different batches of the composition.

The Kava root used in the composition may be obtained specifically from a Vanuatu strain of *Piper methysticum*, which is known for its high quality and potency. The use of this specific strain ensures optimal anxiolytic and analgesic effects in the composition. Other strains may be substituted at different amounts to ensure specific kavalactone concentrations. Further, extracts from the Vanuatu strain or other strains, with 30-60% kavalactones can be used to provide a more consistent batch quality.

The composition may be formulated for administration in a dose-response titration, starting at 1-3 teaspoons and increasing by 0.1-0.5 teaspoon increments until a therapeutically effective reduction in pain is achieved. This titration method allows for personalized dosing to meet the unique needs of each individual subject.

The embodiments described herein are given for the purpose of facilitating the understanding of the present invention and are not intended to limit the interpretation of the present invention. The respective elements and their arrangements, materials, conditions, shapes, sizes, or the like of the embodiment are not limited to the illustrated examples but may be appropriately changed. Further, the constituents described in the embodiment may be partially replaced or combined together.

What is claimed is:

1. A pharmaceutical composition for treating pain and reducing opioid use comprising:

a) 0.5 to 2.5 grams of Red Borneo Kratom or Red Bali Kratom;
b) 0.5 to 2.5 grams of Green Maeng Da Kratom or Green Malay Kratom;
c) 0.5 to 2.5 grams of Kava root from a Vanuatu strain;
d) 0.5 to 2.5 grams of Curcumin or a Curcumin extract;
e) 0.1 to 1.0 grams of Baicalin or a Baicalin extract;
f) 5 to 25 milligrams of Piperine or a Piperine extract;
g) 10 to 100 milligrams of Cannabidiol (CBD) or a CBD extract;
h) 100 to 800 milligrams of L-Theanine; and
i) 100 to 600 milligrams of Quercetin or a Quercetin extract;

wherein the Red Borneo Kratom and Green Maeng Da Kratom are included for daytime pain relief and alertness; the Red Bali Kratom and Green Malay Kratom are included for nighttime pain relief and sleep induction; and the composition is formulated for oral administration in an amount effective to reduce pain and opioid use in a subject in need thereof.

2. The pharmaceutical composition of claim 1, wherein the Curcumin is present as a Curcumin extract standardized to contain 90-99% curcuminoids.

3. The pharmaceutical composition of claim 1, wherein the Baicalin is present as a Baicalin extract from *Scutellaria baicalensis* root.

4. The pharmaceutical composition of claim 1, wherein the L-Theanine is present as pure L-Theanine.

5. The pharmaceutical composition of claim 1, wherein the Quercetin is present as a Quercetin extract from *Sophora japonica* standardized to contain 90-99% quercetin.

6. The pharmaceutical composition of claim 1, wherein the composition is formulated as a powder for reconstitution in a liquid.

7. The pharmaceutical composition of claim 1, wherein the composition is formulated in a dosage form selected from the group consisting of a tablet, capsule, softgel, liquid solution, and liquid suspension.

8. The pharmaceutical composition of claim 1, wherein the composition is further effective to reduce symptoms associated with opioid withdrawal or opioid use disorder in the subject.

9. The pharmaceutical composition of claim 1, wherein the composition is further effective to reduce anxiety in the subject.

10. The pharmaceutical composition of claim 1, wherein the composition is further effective to improve sleep quality in the subject.

11. A method of treating pain and reducing opioid use in a subject in need thereof, comprising administering to the subject a therapeutically effective amount of the composition of claim 1.

12. A method for reducing pain and opioid use in a subject in need thereof, the method comprising administering to the subject an effective amount of a composition comprising:

a) 0.5-2.5 grams of a first *Mitragyna speciosa* powder selected from the group consisting of Red Borneo Kratom, Green Maeng Da Kratom, Red Bali Kratom, and Green Malay Kratom;
b) 0.5-2.5 grams of a second *Mitragyna speciosa* powder selected from the group consisting of Red Borneo Kratom, Green Maeng Da Kratom, Red Bali Kratom, and Green Malay Kratom, wherein the second *Mitragyna speciosa* powder is different from the first *Mitragyna speciosa* powder;
c) 0.5-2.5 grams of a *Piper methysticum* from a Vanuatu strain;
d) 0.5-2.5 grams of a *Curcuma longa* extract comprising 50-95% curcuminoids;
e) 0.1-1.0 grams of a *Scutellaria baicalensis* extract comprising 30-90% baicalin;
f) 5-50 milligrams of a *Piper nigrum* extract comprising 85-99% piperine;
g) 10-100 milligrams of a *Cannabis sativa* extract comprising 90-99.9% cannabidiol (CBD);
h) 100-600 milligrams of L-theanine;
i) 100-500 milligrams of a *Sophora japonica* extract comprising 85-99% quercetin; and optionally j) 100-1000 milligrams of 4-amino-3-phenylbutanoic acid (phenibut) and 100-1000 milligrams of a *Valeriana officinalis* extract; wherein the ratio of components a):b):c):d):e):f):g):h):i) is 1:1:1:1:0.2-0.8:0.01-0.1:0.02-0.2:0.2-1.2:0.2-1 by weight;

and wherein administration of the composition results in at least a 30-60% reduction in pain as measured by a visual analog scale and enables a reduction or elimination of opioid use by the subject.

* * * * *